United States Patent [19]

Schechtman et al.

[11] Patent Number: 5,648,452
[45] Date of Patent: Jul. 15, 1997

[54] POLYMERIZATION OF BETA-SUBSTITUTED-BETA-PROPIOLACTONES INITIATED BY ALKYLZINC ALKOXIDES

[75] Inventors: Lee Arnold Schechtman, Fairfield; Joseph Jay Kemper, Cincinnati, both of Ohio

[73] Assignee: The Procter & Gamble Company, Cincinnati, Ohio

[21] Appl. No.: 447,136

[22] Filed: Jun. 1, 1995

Related U.S. Application Data

[63] Continuation of Ser. No. 341,808, Nov. 18, 1994, abandoned, which is a continuation-in-part of Ser. No. 189,015, Jan. 28, 1994, abandoned.

[51] Int. Cl.$^6$ ............................ C08G 63/08; C08G 63/84
[52] U.S. Cl. ........................... 528/357; 528/354; 528/361
[58] Field of Search .................................. 528/354, 357, 528/361

[56] References Cited

U.S. PATENT DOCUMENTS 5,023,316  6/1991  Benvenuti et al. ................... 528/357

FOREIGN PATENT DOCUMENTS

0601885A2  6/1994  European Pat. Off. .

OTHER PUBLICATIONS

Hans R. Kricheldorf et al., "Polylactones 20, Polymerization of E–Caprolactone with Tributyltin Derivatives: A Mechanistic Study", Macromolecules 24:1944–1949 (Apr. 1991).

Kricheldorf et al., "Anionic and Pseudoanionic Polymerization of Lactones—A Comparison" Makromol. Chem., Macromol. Symp. 32:285–298 (Apr. 1990).

Hans R. Kricheldorf et al., "Poly(lactones) 9 Polymerization Mechanism of Metal Aykoxide Initiated Polymerizations of Lactide and Various Lactones", (Jan 1988).

Aida, T., Y. Maekawa, S. Asano and S. Inoue, "Immortal" Polymerization. Polymerization of Epoxide and β–Lactone with Aluminum Prophyrin in the Presence of Protic Compound, Macromolecules, vol. 21, No. 5, pp. 1195–1202 (May 1988).

Agostini, D.E., J.B. Lando & J.R. Shelton, "Synthesis and Characterization of Poly–β–hydroxybutyrate. I. Synthesis of Crystalline DL–poly–β–hydroxybutyrate from DL–β–butyrolactone", Journal Of Polymer Science, Part A–1, vol. 9, No. 10, pp. 2775–2787 (Oct. 1971).

Bero, M., J. Kasperczyk & G. Adamus, "Coordination of Polymerization of Lactides, 3", Makromol. Chem. vol. 194, No. 3, pp. 907–912 (Mar. 1993).

Billingham, N.C., M.G. Proctor & J.D. Smith, "Polymerization and Copolymerization of β–butyrolactone by Aluminum Compounds", Journal Organometallic Chemistry, vol. 341, No. 1–3, pp. 83–93 (Mar. 1988).

Dubois, P., I. Barakat, R. Jérôme & P. Teyssié, "Macromolecular Engineering of Polylactones and Polylacides. 12. Study of the Depolymerication Reactions of Poly(e–caprolactone) with Functional Aluminum Alkoxide End Groups", Macromolecules, vol. 26, No. 17, pp. 4407–4412 (Aug. 1993).

Gross, R.A., Y. Zhang, G. Konrad & R.W. Lenz, "Polymerization of 62–monosubstituted–β–propiolactones Using Trialkylaluminum–water Catalytic Systems and Polymer Characterization", Macromolecules, vol. 21, No. 9, pp. 2657–2668 (Sep. 1988).

Hocking, P.J. & R.H. Marchessault, "Syndiotactic Poly[(R, S)–β–hydroxybutyrat] Isolated from Methylaluminoxane–catalyzed Polymerization", Polymer Bulletin, vol. 30, No. 2, pp. 163–170 (Feb. 1993).

Inoue, S., Y. Tomoi, T. Tsuruta & J. Furukawa, "Organometallic–catalyzed Polymerization of Propiolactone", pp. 229–233, (May, 1961).

Hori, Y., M. Suzuki, A. Yamaguchi & T. Nishishita, "Ring–opening Polymerization of Optically Active 62–butyrolactoone Using Distannoxane Catalysts: Synthesis of High Molecular Weight Poly(3–hydroxybutyrate)", Macromolecules, vol. 26, No. 20, pp. 5533–5534 (Sep. 1993).

Kaspercayk, J. & M. Bero, "Coordination Polymerization of lactides, 4", Makromol. Chem., vol. 194, No. 3, pp. 913–925 (Mar. 1993).

Kemnitzer, J.E., S.P. McCarthy & R.A. Gross, "Preparation of Predominantly Syndiotactic Poly(β–butyrolactone)", Macromolecules, vol. 26, No. 6, pp. 1221–1229 (Mar. 1993).

Kricheldorf, H.R., M.V. Sumbél and I. Kreiser–Saunders, "Polylactones. 20. Polymerization of e–Caprolactone with Tributyltin Derivatives: A Mechanistic Study", Macromolecules, vol. 24, pp. 1944–1949 (no month identified 1991).

Kricheldorf, H.R., I. Kreiser–Saunders and N. Scharnagl, "Anionic and Pseudoanionic Polymerization of Lactones—A Comparison", Makromol. Chem. Macromol. Symp., vol. 32, pp. 285–298 (no month identified 1990).

Kricheldorf, H.R., M. Beri and N. Scharnagl, "Poly(lactones). 9. Polymerization Mechanism of Metal alkoxide Initiated Polymerizations of Lactide and Varous Lactones", Macromolecules, vol. 21, pp. 286–293 (no month identified 1988).

Kumagai, Y. & Y. Doi, "Synthesis of a Block Copolymer of Poly(3–hydroxybutyrate) and Poly(Ethylene Glycol) and Its Application to Biodegradable Polymer Blends", Journal Of Environmental Polymer Degradation, vol. 1, No. 2, pp. 81–87 (Apr./Jun. 1993).

(List continued on next page.)

*Primary Examiner*—Shelley A. Dodson
*Attorney, Agent, or Firm*—Braham J. Corstanje; Karen F. Clark; David L. Suter

[57] ABSTRACT

The present invention relates to a method of preparing a polyester comprising polymerizing at least one β-substituted-β-propiolactone in the presence of an initiating amount of alkylzinc alkoxide in bulk or in solvent for a reaction time and temperature sufficient to produce said polyester.

26 Claims, No Drawings

OTHER PUBLICATIONS

Le Borgne, A. & N. Spassaky, "Stereoelective Polymerization of β-butyrolactone", *Polymer*, vol. 30, No. 12, pp. 2312–2319 (Dec. 1989).

"Living Polymerization and Selective End Functionalization of e-Caprolactone Using Zinc Alkoxides as Initiators", *Macromolecules*, vol. 24, No. 24, pp. 6542–6545 (Nov. 1991).

Shelton, J.R., D.E. Agostini & J.B. Lando, "Synthesis and Characterization of Poly-β-hydroxybutyrate. II. Synthesis of D-poly-β-hydroxybutyrate and the Mechanism of Ring-opening Polymerization of β-butyrolactone", *Journal of Polymer Science*, Part A–1, vol. 9, No. 10, pp. 2789–2799 (Oct. 1971).

Tanahashi, N. & Y. Doi, "Thermal Properties and Stereoregularity of Poly(3-hydroxybutyrate) Prepared from Optically Active β-butyrolactone With a Zinc-based Catalyst", *Macromolecules*, vol. 24, No. 20, pp. 5732–5733 (Sep. 1991).

Zhang, Y. R.A. Gross & R.W. Lenz, "Stereochemistry of the Ring-opening Polymerization of (S)-β-butyrolactone", *Macromolecules*, vol. 23, No. 13, pp. 3206–3212 (Jun. 1990).

POLYMERIZATION OF BETA-SUBSTITUTED-BETA-PROPIOLACTONES INITIATED BY ALKYLZINC ALKOXIDES

This is a continuation of application Ser. No. 08/341,808, filed on Nov. 18, 1994 abandoned, which is a continuation-in-part of application Ser. No. 08/189,015, filed on Jan. 28, 1994, now abandoned.

TECHNICAL FIELD

The present invention relates to a method of polymerizing β-lactones in the presence of an organometallic initiator. More specifically, the invention relates to a method of polymerizing at least one β-substituted-β-propiolactone in the presence of an alkylzinc alkoxide.

BACKGROUND

β-substituted-β-propiolactone polymers are made by a wide variety of bacteria to serve as a source of both energy and carbon supply. Perhaps the best known of these bacterially produced polyesters is poly(β-hydroxybutyrate) (PHB) characterized by a structure having a repeat unit of the formula:

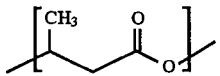

The bacterially-produced form of poly(β-hydroxybutyrate) is a highly crystalline, optically active and perfectly isotactic polyester.

Ring-opening polymerization of β-substituted-β-lactones in the presence of organometallic catalysts to produce β-substituted-β-propiolactone polymers is known. The use of alkylaluminum-water based polymerization initiators or catalysts is described by Benvenuti and Lenz in U.S. Pat. No. 5,023,316 and others (for example see Agostini, D. E.; Lando, J. B.; Shelton, J. R. *J. POLYM. Sci.* PART A-1 1971, 9[A], 2775–2587 and 2789–2799; Gross, R. A.; Zhang, Y.; Konrad, G.; Lenz, R. W. *MACROMOLECULES* 1988, 21, 2657–2668). Polymerization of β-butyrolactone with aluminum porphyrins is described by Aida, T.; Maekawa, S.A. and Inoue, S. in Macromolecules 1988, 21, 1195–1202. The use of polymerization initiators derived from organotin compounds is described by Kemnitzer, J. E.; McCarthy, S. P.; Gross, R. A. in *MACROMOLECULES* 1993, 26, 1221–1229 and Hori, Y.; Suzuki, M.; Takahashi, Y.; Yamaguchi, A.; Nishishita, T. in *MACROMOLECULES* 1993, 26, 5533–5534. The use of organozinc-water based initiators for the polymerization of β-substituted-β-lactones is reported by Zhang, Y.; Gross, R.A.; and Lenz, R.W. in *MACROMOLECULES* 1990, 23, 3206–32–12 and Tanahashi, N.; Doi, Y. in *MACROMOLECULES* 1991, 24, 5732–5733. Le Borgne, A. and Spassky, N in *POLYMER* 1989, 30, 2312–2319 describe the use of a chiral alkylzinc alkoxide initiator for the polymerization of racemic β-butyrolactone. Kumagai, Y. and Doi, Y. in *J. ENVIRON. POLYM. DEGRADN.* 1993, 1, 81–87 describe the use of a zinc-water-polymeric alcohol initiator for the polymerization of this same monomer.

A disadvantage of each of the above systems mentioned for the polymerization of β-substituted-β-propiolactones to polyesters is that each system requires either long reaction times, production of low yields of polymer, limited to lower molecular weight polyester products, broad molecular weight distributions, production of mixtures of isotactic, atactic, and/or syndictactic polymer, or combinations of these deficiencies.

The alkylaluminum-water systems cited above are commonly referred to as "aluminoxane" catalysts or initiators. The yield of polyester produced from β-substituted-β-propiolactones when these initiators are used is generally in the range of 20–60% crude yield after 7–14 days with the product having a molecular weight distribution or polydispersity, weight-average molecular weight (Mw) divided by number-average molecular weight (Mn) of around 15 (see Gross, R. A.; Zhang, Y.; Konrad, G.; Lenz, R. W. *MACROMOLECULES* 1988, 21, 2657–2668). The use of aluminum porphyrin initiators (see Aida, T.; Maekawa, S.A. and Inoue, S. in *MACROMOLECULES* 1988, 21, 1195–1202) will produce poly(β-butyrolactone) from β-butyrolactone with essentially quantitative yields and very narrow polydispersity (1.08–1.16), but the highest reported molecular weights of the polyester are less than 10,000 and the reaction times required are 5 to 20 days.

The use of distannoxane initiators (see Hori, Y.; Suzuki, M.; Takahashi, Y.; Yamaguchi, A.; Nishishita, T. in *MACROMOLECULES* 1993, 26, 5533–5534) is useful for the polymerization of racemic β-butyrolactone, [S]-β-butyrolactone, or [R]-β-butyrolactone to high molecular weight polymer (Mw>100,000) near quantitative yield in 4 h at 100° C. The polydispersity of such produced poly(β-butyrolactone) is typically 1.7–2.7. Syndiotactic poly(β-butyrolactone) is produced when tributyltin methoxide is used to initiate the polymerization of racemic β-butyrolactone (see Kemnitzer, J. E.; McCarthy, S. P.; Gross, R. A. in *MACROMOLECULES* 1993, 26, 1221–1229). The yields of polyester are 24–69% after 13–18 days and the molecular weights below 10,000 with the polydispersities are typically 1.04–1.12.

Polymerization of β-substituted-1β-propiolactones with dialkylzinc-water initiators require 5–7 days (see Zhang, Y.; Gross, R. A.; and Lenz, R.W. in *MACROMOLECULES* 1990, 23, 3206–32–12 and Tanahashi, N.; Doi, Y. in *MACROMOLECULES* 1991, 24, 5732–5733). Yields of polymer are generally 57–84%, but can reach 100% with racemic β-butyrolactone. The polyester molecular weights are reported up to 50,000 with polydispersities typically 1.1–1.5. Unfortunately, the nature of the initiator is not well defined and the actual monomer-initiator ratio used is hard to quantitate.

The use of diethylzinc-[R]-(–)-3,3-dimethyl-1,2-butanediol to initiate the polymerization of racemic β-butyrolactone in bulk leads to polyester with enhanced isotacticity (see Le Borgne, A. and Spassky, N. in *POLYMER* 1989, 30, 2312–2319). The reaction times are short, 2.5–15 h, and the yield can be as high as 84%. However, the molecular weight of the product, especially for the higher yield reaction (<3,000), is very low.

Ring-opening polymerization of lactones other than β-propiolactones with alkylzinc alkoxide initiators are known. The polymerization of ε-caprolactone and lactides are reported in the literature (see Barakat, L; DuBois, Ph,; Jerome, R.; and Teyssie, Ph. in *MACROMOLECULES* 1991, 24, 6542–6545). Specifically, the use of ethylzinc isopropoxide is reported to copolymerize s-caprolactone and L,L-lactide (see Bero, M.; Kasperczyk, J.; and Adamus, G. in *Makromol Chem.* 1993, 194, 907–912 and 913–925). Molecular weights of these copolyesters are over 100,000 with polydispersities of 1.4, and the yields range from 60–89%. These polymerizations require 2.5–21 days at temperatures between 50 and 100° C. Also, these investigators found that above 50° C. the zinc initiators also are effective transesterification catalysts.

The use of a chiral diol-ethylzinc initiator has been disclosed for the polymerization of racemic β-butyrolactone as described above (Le Borgne, A. and Spassky, N. in *POLYMER* 1989, 30, 2312–2319).

The previous attempts to polymerize β-substituted-β-propiolactones in the presence of various initiators have generally resulted in less than optimum product yields and length of reaction times.

Based on the foregoing, there is a need to provide a method of polymerizing β-substituted-β-propiolactones in the presence of an initiator which results in an improved yield of the desired polymer and/or an improved reaction time.

SUMMARY

The present invention relates to a method of preparing a polyester comprising polymerizing at least one β-substituted-β-propiolactone in the presence of an initiating amount of alkylzinc alkoxide in bulk or in solvent for a reaction time and temperature sufficient to produce said polyester.

DETAILED DESCRIPTION

As used herein, "alkyl" means a saturated carbon-containing chain which may be straight or branched; and substituted (mono-or poly-) or unsubstituted.

As used herein, "aryl" means an aromatic; substituted (mono-or poly-) or unsubstituted, preferably unsubstituted. Preferred aryls are phenyl and napthyl; more preferred is phenyl.

As used herein, "aralkyl" means an alkyl substituted with aryl (e.g., benzyl).

As used herein, "alkaryl" means an aryl substituted with alkyl (e.g., 4-methylphenyl).

As used herein, "alkenyl" means a carbon-containing chain which may be monounsaturated (i.e., one double bond in the chain) or polyunsaturated (i.e., two or more double bonds in the chain); straight or branched; and substituted (mono-or poly-) or unsubstituted.

As used herein, "cycloalkyl" means a cyclic alkyl (e.g., cyclohexyl).

As used herein, "comprising" means that other steps and other ingredients which do not affect the end result can be added. This term encompasses the terms "consisting of" and "consisting essentially of".

As used herein, "initiator" means an agent used to start the polymerization of a monomer.

As used herein, "an initiating amount" means a sufficient amount of an initiator to commence the chemical reaction for polymerization. In a preferred embodiment, the initiating amount of initiator of the present invention for carrying out a polymerization reaction of the present invention is from about 0.005 mole % to about 1 mole %; more preferably from about 0.01 mole % to about 0.5 mole %.

As used herein, "in bulk" refers to polymerization without added solvent.

The present invention answers the need for an improved method of preparing β-substituted-β-propiolactone polymers. The present invention relates to a method of preparing a polyester comprising polymerizing at least one β-substituted-β-propiolactone in the presence of an initiating amount of alkylzinc alkoxide in bulk or in solvent for a reaction time and temperature sufficient to produce said polyester.

The β-propiolactone is substituted at the β position by any conventional non-interfering substituent. Suitable substituents include organic residues, halo, nitro, and the like. Suitable organic residues include hydrocarbon residues, either unsubstituted or substituted, suitable substituents for such substituted hydrocarbon residues include halo and nitro, oxygen or sulfur-containing organic residues such as ether residue or a carboalkoxy group (—COOR') wherein R' is alkyl. Suitable hydrocarbon residues include alkyl, alkenyl, aryl, aralkyl, alkaryl, and cycloalkyl. Substituents containing up to 19 carbon atoms, particularly hydrocarbon substituents, are preferred. The β-substituted-β-propiolactones are represented by the structural formula:

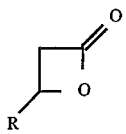

wherein R is the non-interfering substituent. The β-substituted-β-propiolactone polyester produced by the present method has a repeat unit having the formula:

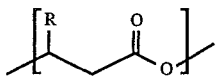

where R is the non-interfering substituent.

The polyesters formed by the method disclosed herein are useful as biodegradable and general thermoplastic materials, for example, as biocompatible materials in medical applications and in drug delivery systems for the controlled release of pharmaceuticals in the body. Biodegradable polyesters formed by the method disclosed herein preferably are predominantly of [R] configuration.

The method of the present invention involves polymerizing at least one β-substituted-β-propiolactone in the presence of an initiating amount of simple alkylzinc alkoxide in bulk or a solvent for the β-substituted-β-propiolactone(s) and for the initiator for a time and at a temperature sufficient to produce the polyester.

The alkylzinc alkoxide initiator useful in the present invention is known. The structure of the initiator has the formula:

where $R^1$ and $R^2$ are independently a $C_1$, $C_2$, $C_3$, $C_4$, $C_5$, $C_6$, $C_7$, $C_8$, $C_9$, or $C_{10}$ alkyl.

In a preferred embodiment of the present invention, the initiator is a nonchiral alkylzinc alkoxide; more preferably the initiator is ethylzinc isopropoxide, methylzinc isopropoxide, ethylzinc ethoxide, or ethylzinc methoxide; more preferably still, ethylzinc isopropoxide.

When the polymerizing is conducted in a solvent for the initiator and for the β-substituted-β-propiolactone(s), the solvent is preferably an aryl hydrocarbon comprising from about 6 to about 15 carbons or alkyl hydrocarbon comprising from about 5 to about 18 carbons; more preferably toluene or xylene.

In a manner similar to that disclosed in several publications (see Le Borgne, A. and Spassky, N. in *POLYMER* 1989, 30, 2312–2319; Barakat, I.; DuBois, Ph.; Jerome, R.; and Teyssie, Ph. in *MACROMOLECULES* 1991, 24, 6542–6545, or Herold, R.J.; Aggarwal, S.L.; and Neff, V. in *CANADIAN J. CHEM.* 1963, 41, 1368–1380) the initiator, alkylzinc alkoxide is prepared by slow addition of the alcohol to a solution of dialkylzinc in aliphatic hydrocarbon solvent such as hexane or aromatic hydrocarbons such as toluene. The initiator solution can then be used directly or the initiator can be isolated from solvent as a solid.

All initiator preparations disclosed herein are conducted in glassware which had been flame dried while being flushed with argon and finally maintained under a positive pressure of argon. Transfers of the initiator solutions are carried out either by cannulation or with a syringe, under an argon atmosphere. Transfers of the initiator powders are carried out in a drybox under an inert atmosphere. The alcohol for the initiator preparation is typically dried by reflux over sodium metal, followed by distillation under an argon atmosphere. The diethylzinc used to prepare the initiator is obtained as a solution in hydrocarbon solvent, hexane or toluene, and used in this solvent.

In each of the following examples the following basic procedure, unless otherwise noted, is used to prepare the polymer. The ampules to be used for the polymerization are septum capped, and flame dried while flushing with argon. All reactants added to the ampules are transferred with a syringe under an argon atmosphere. All β-substituted-β-propiolactone monomers are dried by several distillations from calcium hydride under vacuum prior to use. Enantiomerically pure [S]-β-butyrolactone is synthesized by the method of Seebach (see Müller, J.-M.; Seebach, D. ANGEW. CHEM. INT. ED. ENGL. 1993, 32, 477–502 ; Breitschuh, R.; Seebach, D. CHIMIA 1990, 44, 216–218 ; Züger, M.; Seebach, D. HELV. CHIM. 1982, 49, 495–503 ; and Griesbeck, A.; Seebach, D. HELV. CHIM. 1982, 70, 1320–1325). [R]-β-butyrolactone can be obtained by several published methods (see Pommier, A.; Pons, J-M. Synthesis 1993, (5), 441–459; Ohta, T.; Miyake, T.; Takaya, H. J. Chem. Soc., Chem. Commun. 1992, 1725–26). The monomer is purified by fractional and spinning-band distillations under vacuum prior to the distillation from calcium hydride. The appropriate monomer is transferred into the ampule. If solvent is used, it is added to the ampule and then the initiator solution is added. Polymerization reactions in the ampules are carried out as noted between 20° and 100° C. for time periods ranging from 3 hours to 10 days, more preferably from about 3 hours to about 4 days, for homopolymerizations and copolymerizations. The crude products are clear, colorless viscous liquids or white solids depending on whether racemic or enantiomerically enriched monomers were used. The ampules are opened at the end of the polymerization reaction periods and bulk reaction products are taken up into chloroform and recovered by precipitation into ether-hexane (3:1) mixture. The polymer is dried under vacuum.

Depending upon one's source of monomer and the desired molecular weight of the monomer, one may wish to take steps to further purify the monomer. For example, racemic β-butyrolactone may be further purified as follows. Racemic β-butyrolactone is distilled several times from $CaH_2$ under reduced pressure with the final distillation onto neutral alumina (activity I), which is flamed under vacuum prior to the distillation, and the monomer is stored over this alumina. Just prior to polymerization, depending on whether the polymerization is to be a bulk or solution polymerization, either the neat monomer or a solution of the monomer is passed through an alumina column under dry argon directly into the polymerization vessel.

Enantiomerically enriched monomer (i.e., [R]-β-butyrolactone or [S]-β-butyrolactone) may be further purified as follows. The monomer is distilled from $CaH_2$. It is then chromatographed on neutral alumina (activity I) with pentane as eluent. The fractions are analyzed by gas chromatography for purity and the middle cuts are combined and distilled from $CaH_2$ onto alumina, stored over alumina, and passed through an alumina column as described above for the racemic monomer.

For selected samples the molecular weights, and melting temperature (Tm) are given. Melting temperatures are determined by differential scanning calorimetry (DSC). Molecular weight determinations are made by gel permeation chromatography (GPC) and molecular weights are reported in terms of the number average (Mn) and weight average (Mw) molecular weights. The polydispersities or ratio of Mw to Mn are also reported. $^1H$ and $^{13}C$ NMR spectra are obtained for the various products to assist in the determination of the structures by measuring stereoregularity and tacticity effects of the polymers produced. In the case of the copolymers, the $^1H$ NMR spectra is useful in determining the copolymer compositions. Yields of the various products are also reported in the tables which follow after the Examples.

All molecular weight data reported in the Tables which follow are obtained by GPC using either three Phenogel or Ultrastyragel linear 5 μm columns (one 50×7.8 mm and two 300×7.8 mm) in series. A refractive index detector is used. Samples are prepared at 0.2% in $CHCl_3$, which is also the mobile phase (1.00 mL/min). Calibration is performed with narrow polystyrene standards and data analyzed using Waters Expert Ease software. NMR spectra were recorded on either a General Electric QE-300 or a Bruker AC-300 (at 300 MHz for $^1H$ spectra) in deuteriochloroform. Chemical shifts are reported in ppm from a TMS internal standard. $^{13}C$ NMR measurements are recorded at 75.4 MHz. All spectra are recorded at 25°–30° C. and $CDCl_3$ and tetramethylsilane (TMS) are used as internal references for $^{13}C$ and $^1H$ NMR spectra, respectively.

Melting temperatures (Tm) for polymer samples are determined with a Mettler T3000 system and the data processed with Merrier GraphWare TA72 software. The sample is heated at 10° C./min. The melt temperature (Tm) is reported as the peak maximum, and the glass transition temperature (Tg) is reported as the transition mid-point.

The process of the present invention may be carried out using as monomer(s) a single β-substituted-β-propiolactone to produce a homopolymer or a mixture of different β-substituted-β-propiolactones to produce a copolymer. The molar ratio of zinc to monomers in the initial reaction solution will range from 0.00005 to 0.05, more preferably from 0.0005 to 0.01. Yield of product generally increases with higher levels of initiator in the reaction mixture. The initial monomer concentration in the solvent can vary widely. The use of approximately equal volumes of solvent and monomer is suitable, but no solvent except that introduced with the initiator if any is necessary.

The reaction temperature will preferably be in the range of 20° C. to 80° C., more preferably from about 40° C. to about 80° C., more preferably from about 45° C. to about 60° C. If a faster reaction time is desired, the temperature is preferably from about 70° C. to about 80° C., more preferably about 75° C. The reaction time will typically range from 17 to 48 hours for both homopolymerization and copolymerization reactions. However, the time may be as short as 3 hours and as long as 10 days or more.

In each of Examples 1–6 and 10, the monomer used is racemic [R,S]-β-butyrolactone (BL) and the initiator is ethylzinc isopropoxide used in an amount as indicated. In Examples 7 and 8 [S]-β-butyrolactone is used. Example 9 is a copolymerization of [S]-β-butyrolactone and [S]-β-pentyl-β-propiolactone. In Example 11 [R]-β-butyrolactone is used. Example 12 is a copolymerization of [R]-β-butyrolactone and [R]-β-pentadecyl-β-propiolactone. The reaction is carried out in bulk with no solvent except for the small amount added with the initiator, or carried out in solution.

EXAMPLE 1

An oven-dried and then flamed, dry argon flushed, pyrex tube (16×150 mm) capped with a septum was charged via syringe with 9.77 g (114 mmol) racemic β-butyrolactone. Ethylzinc isopropoxide in toluene (205 μL of 1.1 M solution, 0.225 mmol) was added via syringe. The reaction was allowed to proceed at 50° C. for 40 h. The product, a gum, was cooled and dissolved in $CHCl_3$ and recovered by precipitation into a rapidly stirred ether-hexane mixture (3:1 v/v). The resulting gum was isolated by filtration or simple decantation of the liquid after clarification, and dried under vacuum at room temperature.

EXAMPLE 2

The basic procedure described in Example 1 was followed with 5.72 g (66.5 mmol) racemic β-butyrolactone and ethylzinc isopropoxide in toluene (180 μL of 1.1M solution, 0.198 mmol). Polymerization was carried out at 50° C. for 17 h.

EXAMPLE 3

The basic procedure described in Example 1 was followed with 10.67 g (124.1 mmol) racemic β-butyrolactone and ethylzinc isopropoxide in toluene (335 μL of 1.1M solution, 0.369 mmol). Polymerization was carried out at 20° C. for 46 h.

EXAMPLE 4

The basic procedure described in Example 1 was followed with 7.76 g (90.2 mmol) racemic β-butyrolactone and ethylzinc isopropoxide in toluene (406 μL of 1.1M solution, 0.447 mmol). Polymerization was carried out at 50° C. for 17 h.

EXAMPLE 5

The basic procedure described in Example 1 was followed with 10.25 g (119 mmol) racemic β-butyrolactone and ethylzinc isopropoxide in toluene (536 μL of 1.1M solution, 0.590 mmol). Polymerization was carried out at is 20° C. for 46 h.

EXAMPLE 6

The basic procedure described in Example 1 was followed with 4.84 g (56.3 mmol) racemic β-butyrolactone and ethylzinc isopropoxide in toluene (501 μL of 1.1M solution, 0.551 mmol). Polymerization was carried out at 50° C. for 17 h.

EXAMPLE 7

An oven-dried and then flamed, dry argon flushed, pyrex tube (16×150 mm) capped with a septum was charged via syringe with 2.39 g (27.8 mmol) [S]-β-butyrolactone. Ethylzinc isopropoxide in toluene (51 μL of 1.1M solution, 0.056 mmol) was added via syringe. The reaction was allowed to proceed at 50° C. for 21 h. During this time the liquid in the tube had solidified to a white mass. This solid was dissolved in $CHCl_3$ and recovered by precipitation into a rapidly stirred ether-hexane mixture (3:1 v/v). The resulting solid was isolated by filtration and dried under vacuum at room temperature (2.02 g).

EXAMPLE 8

The basic procedure described in Example 7 was followed with 2.09 g (24.3 mmol) [S]-β-butyrolactone and ethylzinc isopropoxide in toluene (109 μL of 1.1M solution, 0.12 mmol). Polymerization was carried out at 20° C. for 48 h.

EXAMPLE 9

The copolymer derived from [S]-β-butyrolactone and [S]-β-pentyl-β-propiolactone was prepared as described for the homopolymer using 2.07 g (24.0 mmol) β-butyrolactone and 0.187 g (1.32 mmol) β-pentyl-β-propiolactone with ethylzinc isopropoxide (114 μL, 1.1M solution, 0.13 mmol) at 20° C. for 93 h.

EXAMPLE 10

A homopolymer derived from racemic β-butyrolactone was prepared as follows. Racemic β-butyrolactone (12.9 g distilled from $CaH_2$ and stored over neutral alumina) was mixed with toluene (79.0 g distilled from sodium metal) in a dry, septum capped flask. This mixture was transfered via cannula onto a flamed, argon-flushed column of alumina and then directly into the reaction flask via a syringe needle tip on the column after discarding the first several milliliters of solution eluting from the column. The monomer solution (79.5 g solution, 11.2 g monomer, 0.13 mol) was initiated with ethylzinc isopropoxide in toluene (24 μL of 1.1M solution, 0.026 mmol). The reaction was allowed to proceed at 75° C. for 64 h. The solution was then diluted with $CHCl_3$, and the product recovered and dried as described in Example 1.

EXAMPLE 11

A homopolymer derived from [R]-β-butyrolactone was prepared as follows. An oven-dried and then flamed, dry argon flushed, pyrex tube (16×150 mm) capped with a septum was charged by passage through an alumina column (neutral, Activity I) with 5.21 g (60.5 mmol) [R]-β-butyrolactone. Ethylzinc isopropoxide in toluene (33 μL of 1.1M solution, 0.036 mmol) was added via syringe. The reaction was allowed to proceed at 75° C. for 24 h. The product was purified and isolated as described in Example 7.

EXAMPLE 12

A copolymer derived from [R]-β-butyrolactone and [R]-β-pentadecyl-β-propiolactone was prepared as described for the atactic homopolymer in Example 10 using a monomer mixture which was charged as a toluene solution through an alumina column so that 8.72 g (0.101 mol) [R]-β-butyrolactone, 1.47 g (0.0052 mol) [R]-β-pentadecyl-β-propiolactone, and 65.5 g toluene was added. The polymerization was initiated with ethylzinc isopropoxide (48 μL, 1.1M solution, 0.053 mmol) and the reaction was carried out at 75° C. for 42 h.

The polymerization conditions and yields for Examples 1–6 and 10 are shown in Table I and for Examples 7–9 and 11–12 in Table II. The molecular weights (Mn and Mw) from Examples 1–6 and 10 are reported in Table III, and for Examples 6–9 and 11–12 in Table IV. Also reported in Tables III and IV are peak melting temperature (Tm° C.) for isotactic polymers made with [S]-β-substituted-β-propiolactones and with [R]-β-substituted-β-propiolactones.

TABLE I

Polymerization Conditions for Homopolymerization of Racemic β-Butyrolactone

| Example | Temperature °C. | Time h | Zn/monomer mol % | Yield % |
|---|---|---|---|---|
| 1 | 50 | 40 | 0.2 | 94 |
| 2 | 50 | 17 | 0.3 | 90 |
| 3 | 20 | 46 | 0.3 | 87 |
| 4 | 50 | 17 | 0.5 | 100 |
| 5 | 20 | 46 | 0.5 | 94 |
| 6 | 50 | 17 | 1.0 | 90 |
| 10 | 75 | 64 | 0.02 | 95 |

TABLE II

Polymerization Conditions for Homopolymerization and Copolymerizations of [S]-β-Butyrolactone or [R]-β-Butyrolactone

| Example | Temperature °C. | Time h | Zn/monomer mol % | Yield % |
|---|---|---|---|---|
| 7 | 50 | 21 | 0.2 | 85 |
| 8 | 20 | 48 | 0.5 | 54 |
| 9 | 20 | 93 | 0.5 | 75 |
| 11 | 75 | 24 | 0.06 | 84 |
| 12 | 75 | 42 | 0.05 | 97 |

TABLE III

Product Characterization for Examples in Table I

| | Molecular Weight | | |
|---|---|---|---|
| Example | Mn | Mw | Mw/Mn |
| 1 | 45,900 | 49,100 | 1.07 |
| 2 | 29,800 | 32,900 | 1.06 |
| 3 | 31,400 | 34,800 | 1.11 |
| 4 | 23,700 | 25,200 | 1.10 |
| 5 | 22,200 | 23,400 | 1.06 |
| 6 | 12,700 | 14,300 | 1.13 |
| 10 | 218,000 | 345,000 | 1.58 |

TABLE IV

Product Characterization for Examples in Table II

| | Molecular Weight | | | Tm |
|---|---|---|---|---|
| Example | Mn | Mw | Mw/Mn | °C. |
| 7 | 36,600 | 49,900 | 1.36 | 179 |
| 8 | 3,470 | 5,240 | 1.51 | 160 |
| 9 | 5,150 | 5,150 | 1.62 | 140 |
| 11 | 116,000 | 226,000 | 1.94 | — |
| 12 | 146,000 | 210,000 | 1.43 | 145 |

The copolymer composition of the product of Example 9 is the same as that of the monomer feed (95:5, β-butyrolactone:β-pentyl-β-propiolactone) by $^1$H NMR. Inspection of the carbonyl carbon region of the $_{13}$C NMR spectra show that when racemic monomer is used atactic polymer is obtained, whereas when monomer of high enantiomeric purity is used, polymer of very high to complete isotacticity is produced.

The advantages of this invention are the good control of molecular weight and high yields with relatively short reaction times compared to the existing art cited previously. Also, the tacticity of the polyester produced to with alkylz- inc isopropoxide initiators can be controlled by the optical purity of the monomers used.

All publications mentioned hereinabove are hereby incorporated in their entirety by reference.

It is understood that the examples and embodiments described herein are for illustrative purposes only and that various modifications or changes in light thereof will be suggested to one skilled in the art and are to be included in the spirit and purview of this application and scope of the appended claims.

What is claimed is:

1. A method of preparing a polyester comprising polymerizing at least one β-substituted-β-propiolactone in the presence of an initiating amount of alkylzinc alkoxide for a reaction time and temperature sufficient to produce the polyester, wherein the alkylzinc alkoxide has the structure $R^1ZnOR^2$ wherein $R^1$ and $R^2$ are independently a $C_1$, $C_2$, $C_3$, $C_4$, $C_5$, $C_6$, $C_7$, $C_8$, $C_9$, or $C_{10}$ alkyl.

2. The method of claim 1, wherein the alkylzinc alkoxide is nonchiral.

3. The method of claim 2, wherein the polymerizing is conducted in bulk.

4. The method of claim 2, wherein the polymerizing is conducted in a solvent for the nonchiral alkylzinc alkoxide and for the β-substituted-β-propiolactone.

5. The method of claim 4, wherein the solvent is an aryl hydrocarbon comprising from about 6 to about 15 carbons or alkyl hydrocarbon comprising from about 5 to about 18 carbons.

6. The method of claim 5, wherein the solvent is toluene or xylene.

7. The method of claim 2, wherein the method comprises copolymerizing two different β-substituted-β-propiolactones to produce a copolyester.

8. The method of claim 7, wherein the dissimilar β-substituted-β-propiolactones comprise [S]-β-butyrolactone and [S]-β-alkyl-β-propiolactone wherein the [S]-β-alkyl-β-propiolactone comprises an alkyl group having two or more carbons.

9. The method of claim 7, wherein the dissimilar β-substituted-β-propiolactones comprise [R]-β-butyrolactone and [R]-β-alkyl-β-propiolactone wherein the [R]-β-alkyl-β-propiolactone comprises an alkyl group having two or more carbons.

10. The method of claim 7, wherein the dissimilar β-substituted-β-propiolactones comprise [S]-β-butyrolactone and [R]-β-alkyl-β-propiolactone wherein the [R]-β-alkyl-β-propiolactone comprises an alkyl group having two or more carbons.

11. The method of claim 7, wherein the dissimilar β-substituted-β-propiolactones comprise [R]-β-butyrolactone and [S]-β-alkyl-β-propiolactone wherein the [S]-β-alkyl-β-propiolactone comprises an alkyl group having two or more carbons.

12. The method of claim 2, wherein said β-substituted-β-propiolactone comprises racemic β-butyrolactone.

13. The method of claim 2, wherein the nonchiral alkylzinc alkoxide is ethylzinc isopropoxide, methylzinc isopropoxide, ethylzinc ethoxide, or ethylzinc methoxide.

14. The method of claim 13, wherein the nonchiral alkylzinc alkoxide is ethylzinc isopropoxide.

15. The method of claim 1, wherein the reaction time is about 3 to 100 hours.

16. The method of claim 7 wherein the reaction time is about 3 to 100 hours.

17. The method of claim 1, wherein the temperature is from about 20° C. to about 80° C.

18. The method of claim 17, wherein the temperature is from about 45° C. to about 60° C.

19. The method of claim 7, wherein the temperature is from about 40° C. to about 80° C.

20. The method of claim 18, wherein the temperature is from about 45° C. to about 60° C.

21. The method of claim 1, wherein the temperature is from about 70° C. to about 80° C.

22. The method of claim 7, wherein the temperature is from about 70° C. to about 80° C.

23. The method of claim 1, wherein the alkylzinc alkoxide is present in an amount to give a mole percent range of Zn to β-substituted-β-propiolactone monomers from about 0.005 to about 1.

24. The method of claim 7, wherein the nonchiral alkylzinc alkoxide is present in an amount to give a mole percent range of Zn to β-substituted-β-propiolactone monomers from about 0.005 to about 1.

25. A polyester made by the method of claim 1, wherein the β-substituted-β-propiolactone is substituted with an alkyl comprising from about 1 to about 19 carbons, alkenyl comprising from about 2 to about 19 carbons, aryl comprising from about 6 to about 19 carbons, aralkyl comprising from about 7 to about 19 carbons, alkaryl comprising from about 7 to about 19 carbons, or cycloalkyl comprising from about 3 to about 19 carbons.

26. A copolyester made by the method of claim 7, wherein the two different β-substituted-β-propiolactones are independently substituted with an alkyl comprising from about 1 to about 19 carbons, alkenyl comprising from about 2 to about 19 carbons, aryl comprising from about 6 to about 19 carbons, aralkyl comprising from about 7 to about 19 carbons, alkaryl comprising from about 7 to about 19 carbons, or cycloalkyl comprising from about 3 to about 19 carbons.

* * * * *